United States Patent [19]

Meier et al.

[11] Patent Number: Plant 6,585

[45] Date of Patent: Feb. 7, 1989

[54] KENTUCKY BLUEGRASS

[75] Inventors: Virgil D. Meier, Marysville, Ohio; James K. Turner, Salem, Oreg.; Eugene W. Mayer, Marysville, Ohio

[73] Assignee: The O.M. Scott & Sons Company, Marysville, Ohio

[21] Appl. No.: 55,435

[22] Filed: May 29, 1987

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

A variety of Kentucky bluegrass having a high level of disease resistance, good turf performance, and a very high level of seed yield potential.

1 Drawing Sheet

BACKGROUND

Kentucky bluegrasses have been disclosed in U.S. Plant Pat. No. 3,156 which issued on May 9, 1972; U.S. Plant Pat. No. 3,186 which issued on May 23, 1972; U.S. Plant Pat. No. 4,336 which issued on Nov. 28, 1978; U.S. Plant patent application, Ser. No. 872,537, filed June 10, 1986; U.S. Plant patent application, Ser. No. 910,146, filed Sept. 19, 1986; U.S. Plant patent application, Ser. No. 27,285, filed Mar. 17, 1987 and U.S. Plant patent application, Ser. No. 28,424, filed Mar. 17, 1987.

SUMMARY OF THE VARIETY

The present invention relates to a new and distinct variety of *Poa pratensis* that has been designated Ba 72-441 Kentucky bluegrass.

Ba 72-441 plant material originated by crossing a Kentucky bluegrass plant ("Victa") disclosed in U.S. Plant Pat. No. 3,156, the seed parent, with a Kentucky bluegrass plant ("Windsor") disclosed in U.S. Plant Pat. No. 2,364, the pollen parent. As a result of this breeding, a distinct variety was produced and asexually propagated by rhizomes, tillers and disseminules. Seed of Ba 72-441 was produced first at Marysville, Ohio and later at Gervais, Oreg. This seed was used to plant turf performance evaluation trials.

Asexual reproduction of Ba 72-441 by propagules (tillers and rhizomes) and by disseminules (modified caryopses produced by apomixis) has consistently produced progeny plants indistinguishable from the mother plant.

Ba 72-441 has a number of highly desirable characteristics including a good level of resistance to Helminthosporium spp. that causes leaf spot, melting out and crown rot, *Ustilago striiformis* that causes stripe smut, and Puccinia spp. that causes rust; an attractive leafy turf type growth habit; moderately wide leaf blades; an attractive green color which can be maintained throughout the entire growing season; good turf performance as evidenced by consistently high scores in tests throughout the U.S.A.; and a very high seed yield potential in the bluegrass seed production region of the U.S.A.

In comparison with its seed parent, the new variety has a thinner peduncle, a more narrow and thinner flag leaf, and better winter color. In comparison to the pollen parent, the new variety has fewer seeds per pound and a higher seed yield.

DETAILED DESCRIPTION OF THE VARIETY

Figure 1:
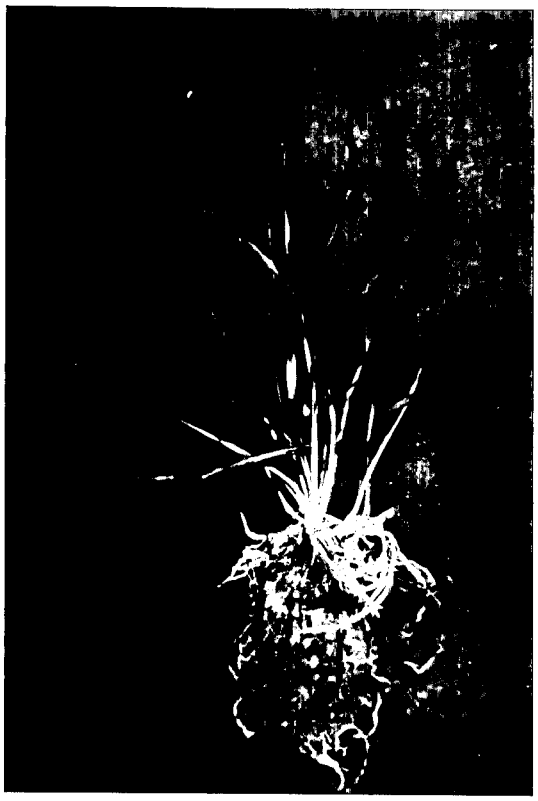
FIG. 1 is a photograph of Ba 72-441 Kentucky bluegrass plant in the vegetative stage including the extensive root and rhizome system.
Figure 2:
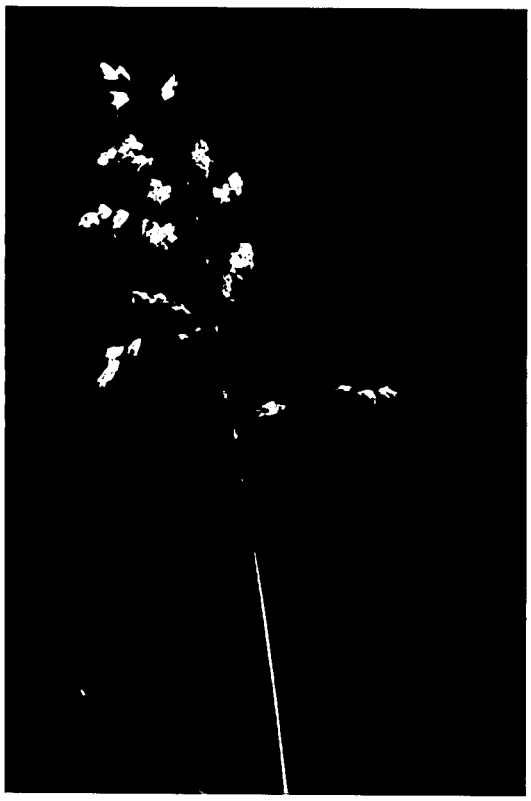
FIG. 2 is a photograph of Ba 72-441 Kentucky bluegrass panicle.
Figure 3:
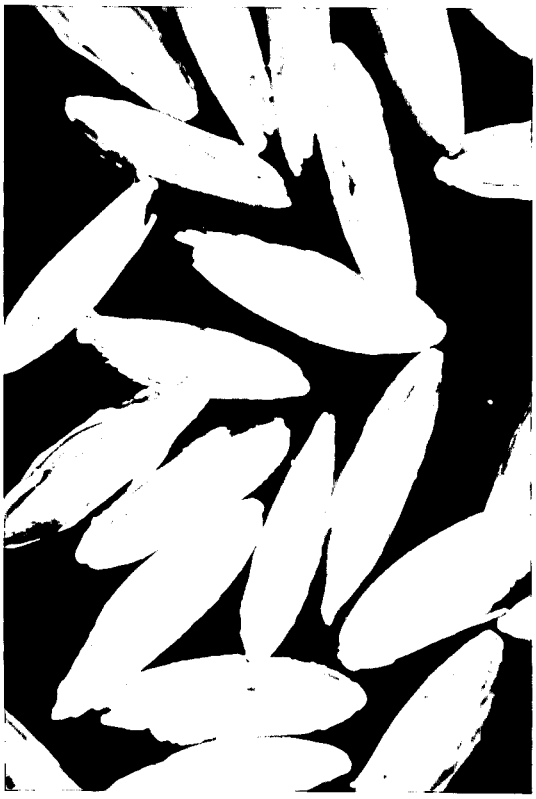
FIG. 3 is a photograph of Ba 72-441 Kentucky bluegrass seed.
Figure 4:
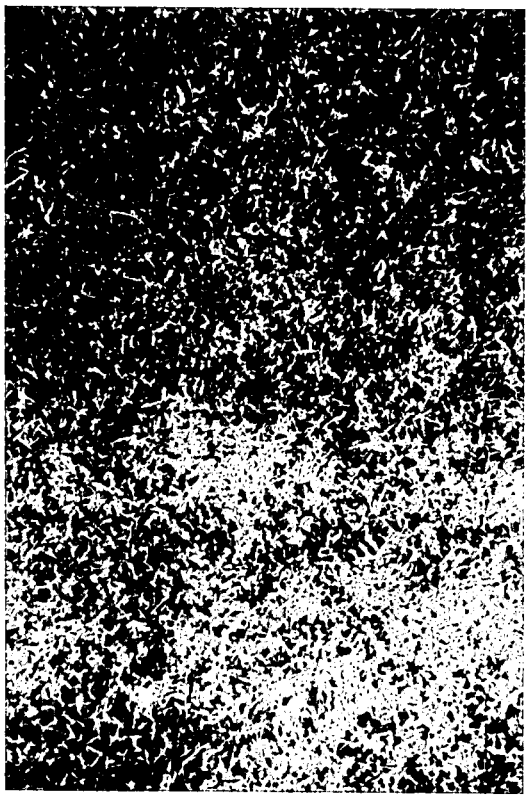
FIG. 4 is a photograph of Ba 72-441 Kentucky bluegrass turf.

Ba 72-441 Kentucky bluegrass (*Poa protensis* L.) is perennial with creeping rhizomes forming a moderately dense turf. When plants overwinter in the field with freezing temperatures and then are brought into the greenhouse during late winter to continue growth undisturbed by clipping under moderate temperatures (60°–80° F.), culms are erect averaging 421 mm in length with an average of 2.7 nodes per culm. The uppermost internode averages 9.3 cm, and the peduncle averages 10.6 cm in length, and 0.558 mm in thickness. The flag leaf averages 4.3 cm in length, 3.3 mm in width and 0.107 mm in thickness. The panicle has an average length of 7.6 cm, width of 4.2 cm, and 5.2 whorls. The lowest whorl has an average of 4.0 branches and the third whorl from the bottom of the panicle has an average of 2.7 branches. The average spikelet at the tip of a branch in the lowest whorl is 5.1 mm in length and has 3.9 florets with an outer glume of 2.9 mm and an inner glume of 3.3 mm in length. A similar spikelet from the third whorl from the bottom of the panicle is 5.0 mm in length and has 3.8 florets with an outer glume of 3.3 mm and an inner glume of 3.3 mm in length. After the seed has been conditioned, the lemma has a generally smooth keel with occasional short hairs and a few long fine hairs at the base. The seed of Ba 72-441 is 3.18 mm in length and 0.88 mm in width with approximately 1,003,037 seeds per pound. Comparisons of Ba 72-441 with other varieties on seed dimensions and on seed numbers per pound are shown in Tables 1 and 2.

TABLE 1

Seed Measurements of Ba 72-441 and Other Bluegrass Varieties After Conditioning.

| Variety | Length (mm) | Width (mm) |
|---|---|---|
| Ba 72-441 | 3.18 | 0.88 |
| Ba 70-139 | 2.86 | 0.78 |

TABLE 1-continued

Seed Measurements of Ba 72-441 and Other Bluegrass Varieties After Conditioning.

| Variety | Length (mm) | Width (mm) |
|---|---|---|
| Ba 72-492 | 2.53 | 0.76 |
| Ba 72-500 | 2.77 | 0.80 |
| Baron | 3.07 | 0.86 |
| Bristol | 2.73 | 0.80 |
| Nassau | 2.96 | 0.78 |
| Newport | 2.76 | 0.71 |
| Park | 3.04 | 0.72 |
| Ram I | 3.51 | 0.84 |
| Victa | 3.20 | 0.86 |
| LSD(.05) | 0.19 | 0.06 |

TABLE 2

Comparison of Seed Numbers Per Pound of Ba 72-441 and Other Bluegrass Varieties After Conditioning.

| | Number of Seeds Per Pound |
|---|---|
| Ba-72-441 | 1,003,037 |
| Ba 70-139 | 1,246,200 |
| Ba 72-492 | 1,275,740 |
| Ba 72-500 | 1,300,105 |
| Adelphi | 1,383,976 |
| America | 1,659,824 |
| Gnome | 1,017,641 |
| Baron | 1,051,693 |
| Birka | 1,223,530 |
| Bonnieblue | 1,135,303 |
| Bristol | 1,270,821 |
| Eclipse | 1,335,668 |
| Glade | 1,108,441 |
| Kenblue | 1,463,923 |
| Merit | 1,109,728 |
| Nassau | 1,127,130 |
| Newport | 1,226,481 |
| Park | 1,248,349 |
| Sydsport | 1,355,644 |
| Vantage | 1,555,303 |
| Victa | 1,038,298 |
| Windsor | 1,520,885 |

Since environmental conditions such as soil and climate may influence morphological characters to some extent, comparisons of morphological characteristics of Ba 72-441 are made with other Kentucky bluegrass varieties in Tables 3–10.

TABLE 3

Morphological Comparison of Panicles of Ba 72-441 and Other Bluegrass Varieties in the Greenhouse at Marysville, Ohio.

| Variety | Panicle Nodding* | Panicle Length (cm) | Panicle Width (cm) | Number of Whorls Per Panicle | Number of Branches Lower Whorl | Number of Branches Third Whorl |
|---|---|---|---|---|---|---|
| Ba 72-441 | 1.4 | 7.6 | 4.2 | 5.2 | 4.0 | 2.7 |
| Ba 70-139 | 2.0 | 6.7 | 3.7 | 4.8 | 3.8 | 2.7 |
| Ba 72-492 | 1.2 | 7.5 | 4.2 | 5.5 | 4.0 | 3.0 |
| Ba 72-500 | 2.0 | 6.8 | 3.8 | 5.0 | 4.0 | 2.4 |
| Baron | 1.0 | 7.8 | 4.1 | 5.2 | 3.8 | 2.5 |
| Bristol | 2.0 | 9.7 | 5.0 | 5.0 | 3.3 | 2.7 |
| Nassau | 2.0 | 10.0 | 6.0 | 5.0 | 3.0 | 2.0 |
| Newport | 2.0 | 10.3 | 4.4 | 4.5 | 2.3 | 2.3 |
| Park | 1.6 | 9.0 | 3.7 | 4.0 | 4.3 | 3.7 |
| Ram I | 2.0 | 9.0 | 4.7 | 4.0 | 2.5 | 2.0 |
| Victa | 1.2 | 7.5 | 4.1 | 5.4 | 4.4 | 3.4 |
| LSD(.05) | 0.5 | 1.6 | 1.0 | 0.8 | 0.7 | 0.8 |

*Panicle nodding rated: 1 = erect, 2 = nodding.

TABLE 4

Morphological Comparison of Spikelets of Ba 72-441 and Other Bluegrass Varieties in the Greenhouse at Marysville, Ohio.

| Variety | Spikelet Length (mm) Lowest Whorl | Spikelet Length (mm) Third Whorl | Number of Florets per Spikelet Lowest Whorl | Number of Florets per Spikelet Third Whorl |
|---|---|---|---|---|
| Ba 72-441 | 5.1 | 5.0 | 3.9 | 3.8 |
| Ba 70-139 | 5.2 | 5.2 | 4.2 | 4.0 |
| Ba 72-492 | 5.2 | 5.0 | 4.4 | 4.2 |
| Ba 72-500 | 5.1 | 5.0 | 4.2 | 3.9 |
| Baron | 5.0 | 5.0 | 3.7 | 3.8 |
| Bristol | 6.2 | 6.0 | 5.7 | 5.3 |
| Nassau | 4.6 | 4.6 | 4.5 | 4.5 |
| Newport | 5.3 | 5.2 | 5.2 | 5.2 |
| Park | 6.5 | 6.7 | 5.2 | 4.7 |
| Ram I | 4.7 | 5.2 | 5.2 | 5.5 |
| Victa | 5.2 | 5.0 | 3.8 | 3.8 |
| LSD(.05) | 0.9 | 0.8 | 1.1 | 1.0 |

TABLE 5

Morphological Comparison of Glumes of Ba 72-441 and Other Bluegrass Varieties in the Greehouse at Marysville, Ohio.

| Variety | Glume Length (mm) Outer Lowest Whorl | Glume Length (mm) Outer Third Whorl | Glume Length (mm) Inner Lowest Whorl | Glume Length (mm) Inner Third Whorl |
|---|---|---|---|---|
| Ba 72-441 | 2.9 | 2.9 | 3.3 | 3.3 |
| Ba 70-139 | 3.2 | 3.1 | 3.5 | 3.5 |
| Ba 72-492 | 2.9 | 3.0 | 3.3 | 3.3 |
| Ba 72-500 | 3.1 | 3.1 | 3.4 | 3.4 |
| Baron | 2.9 | 2.8 | 3.4 | 3.3 |
| Bristol | 3.4 | 3.3 | 3.7 | 3.9 |
| Nassau | 2.3 | 2.4 | 2.7 | 2.7 |
| Newport | 2.6 | 2.5 | 2.9 | 2.9 |
| Park | 3.0 | 3.2 | 3.5 | 3.7 |
| Ram I | 2.6 | 2.4 | 2.9 | 2.7 |
| Victa | 2.8 | 3.0 | 3.3 | 3.3 |
| LSD(.05) | 0.5 | 0.4 | 0.4 | 0.4 |

TABLE 6

Morphological Comparison of Flag Leaves of Ba 72-441 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Ba 72-441 | 4.3 | 3.3 | 0.107 |
| Ba 70-139 | 4.7 | 3.2 | 0.112 |
| Ba 72-492 | 5.2 | 3.6 | 0.117 |
| Ba 72-500 | 4.1 | 3.2 | 0.112 |
| Baron | 4.5 | 3.2 | 0.119 |
| Bristol | 5.5 | 3.4 | 0.127 |
| Nassau | 6.2 | 3.1 | 0.127 |
| Newport | 6.1 | 3.5 | 0.135 |
| Park | 4.2 | 2.6 | 0.109 |
| Ram I | 4.7 | 3.1 | 0.127 |
| Victa | 5.9 | 4.0 | 0.124 |
| LSD(.05) | 1.8 | 0.6 | 0.013 |

TABLE 7

Morphological Comparison of Peduncles, Culms, and Internodes of Ba 72-441 and Other Bluegrass Varieties in the Greehouse at Marysville, Ohio.

| Variety | Peduncle Length (cm) | Peduncle Width (mm) | Culm Length (mm) | Number of Nodes Per Culm | Top Internode Length (cm) |
|---|---|---|---|---|---|
| Ba 72-441 | 10.6 | 0.558 | 421 | 2.7 | 9.3 |
| Ba 70-139 | 13.2 | 0.610 | 435 | 2.7 | 10.2 |
| Ba 72-492 | 12.6 | 0.558 | 486 | 2.2 | 10.5 |
| Ba 72-500 | 12.9 | 0.660 | 439 | 2.7 | 9.8 |
| Baron | 12.7 | 0.559 | 482 | 2.5 | 10.1 |
| Bristol | 15.0 | 0.686 | 522 | 2.7 | 11.3 |

TABLE 7-continued

Morphological Comparison of Peduncles, Culms, and Internodes of Ba 72-441 and Other Bluegrass Varieties in the Greehouse at Marysville, Ohio.

| Variety | Peduncle Length (cm) | Peduncle Width (mm) | Culm Length (mm) | Number of Nodes Per Culm | Top Internode Length (cm) |
|---|---|---|---|---|---|
| Nassau | 8.0 | 0.533 | 450 | 2.5 | 11.2 |
| Newport | 18.0 | 0.558 | 547 | 2.3 | 11.2 |
| Park | 14.3 | 0.787 | 578 | 3.0 | 13.0 |
| Ram I | 18.5 | 0.610 | 527 | 3.0 | 10.2 |
| Victa | 12.2 | 0.711 | 474 | 2.4 | 10.6 |
| LSD(.05) | 3.7 | 0.018 | 79 | 0.6 | 2.1 |

TABLE 8

Morphological Comparison of Leaves of Ba 72-441 and Other Bluegrass Varieties in the Greenhouse at Marysville, Ohio.

| Variety | Ligule Length (mm) | Leaf Length (mm) | Leaf Width (mm) | Leaf Angle (Degrees From Horizontal) |
|---|---|---|---|---|
| Ba 72-441 | 0.23 | 218 | 3.9 | 56 |
| Ba 70-139 | 0.26 | 218 | 4.1 | 55 |
| Ba 72-492 | 0.28 | 239 | 4.4 | 52 |
| Ba 72-500 | 0.25 | 204 | 4.1 | 50 |
| Baron | 0.30 | 313 | 4.4 | 63 |
| Bristol | 0.30 | 253 | 4.3 | 37 |
| Nassau | 0.22 | 226 | 3.5 | 39 |
| Newport | 0.22 | 251 | 4.1 | 50 |
| Park | 0.33 | 329 | 4.2 | 44 |
| Ram I | 0.18 | 188 | 3.7 | 40 |
| Victa | 0.28 | 235 | 4.3 | 52 |
| LSD(.05) | 0.11 | 49 | 0.6 | 10 |

TABLE 9

Morphological Comparison of Leaf Hairs of Ba 72-441 and Other Bluegrass Varieties in the Greenhouse at Marysville, Ohio.

| Variety | Hairs[a] Around Ligule on Upper Surface of the Leaf | Hairs[a] on Collar | Hairs[b] on Ligule |
|---|---|---|---|
| Ba 72-441 | 1.0 | 3.4 | 2.2 |
| Ba 70-139 | 1.0 | 3.5 | 1.5 |
| Ba 72-492 | 1.0 | 3.2 | 1.3 |
| Ba 72-500 | 1.0 | 3.5 | 2.7 |
| Baron | 1.0 | 5.0 | 4.0 |
| Bristol | 1.3 | 4.7 | 4.3 |
| Nassau | 2.7 | 5.0 | 1.0 |
| Newport | 1.0 | 4.0 | 0.8 |
| Park | 1.0 | 1.7 | 0.0 |
| Ram I | 1.0 | 3.7 | 0.3 |
| Victa | 1.0 | 3.3 | 2.2 |
| LSD(.05) | 0.3 | 1.4 | 1.8 |

[a]Hairs around ligule and on collar rated 1-5: 1 = none, 5 = many.
[b]Hairs on ligule rated 0-5: O = none, 5 = many.

TABLE 10

Morphological Comparisons of Ba 72-441 and Other Bluegrass Varieties Grown as Unmowed Spaced Plants in the Field at Marysville, Ohio.

| | Mature Plant Height | Panicle Density | Seedhead Weight |
|---|---|---|---|
| Ba 72-441 | 38 | 7 | 656 |
| Ba 70-139 | 35 | 5 | 402 |
| Adelphi | 42 | 3 | 345 |
| Nugget | 17 | 3 | 233 |
| Bristol | 40 | 4 | 511 |
| Merion | 25 | 2 | 320 |
| Glade | 20 | 3 | 214 |
| Vantage | 52 | 2 | 1019 |

TABLE 10-continued

Morphological Comparisons of Ba 72-441 and Other Bluegrass Varieties Grown as Unmowed Spaced Plants in the Field at Marysville, Ohio.

| | Mature Plant Height | Panicle Density | Seedhead Weight |
|---|---|---|---|
| Victa | 23 | 2 | 648 |

Ratings: Mature Plant Height (cm) includes panicle.
Panicle Density - 1-10, 10 = high panicle density.
Seedhead Weight - Weight (mg) of 3 panicles.

Ba 72-441 has performed well throughout the U.S.A., as exhibited by high turf quality ratings in many different locations in comparison to other varieties. In addition, it has a pleasant medium green color which can be maintained throughout the growing season, good winter color, and early spring greening. Comparisons of Ba 72-441 with other varieties for quality and color are shown in Tables 11-14.

TABLE 11

Comparison of the Turf Quality of Ba 72-441 and Other Bluegrass Varieties in the U.S.A.

| | Adelphia | Lincoln | Maryland | | Marysville, Ohio | |
|---|---|---|---|---|---|---|
| Variety | New Jersey 2 Year Mean | Nebraska 2 Year Mean | Beltsville 1 Year Mean | Accokeek 3 Year Mean | Test 1 5 Year Mean | Test 2 5 Year Mean |
| Ba 72-441 | 6.6 | 6.0 | 5.9 | 2.7 | 2.7 | 2.4 |
| A-34 | | 6.2 | 5.6 | | | |
| Adelphi | 6.4 | 6.1 | 5.9 | 2.4 | 2.7 | |
| Banff | | | 4.8 | | | |
| Baron | 6.4 | 5.6 | 5.3 | 2.4 | | |
| Birka | 5.9 | 5.9 | | 1.8 | | |
| Bonnieblue | 6.7 | 5.8 | 5.0 | 2.3 | | |
| Bono | | | | 1.9 | | |
| Bristol | 6.5 | 5.9 | 5.0 | 2.3 | 2.7 | 2.3 |
| Eclipse | 7.2 | 5.8 | 5.9 | | | |
| Fylking | 5.7 | 6.1 | 4.9 | | | 2.1 |
| Geary | 3.6 | | | | | |
| Glade | 6.7 | 6.4 | 5.3 | | | |
| Kenblue | 3.3 | | | 1.8 | | 2.0 |
| Merion | 6.0 | 5.9 | 5.3 | | | 2.2 |
| Merit | 6.2 | 6.0 | 6.1 | 2.3 | | 2.2 |
| Midnight | 7.3 | 5.9 | 5.5 | 2.4 | | |
| Monopoly | 5.7 | | 4.9 | | | |
| Nassau | 5.9 | | 4.5 | | | |
| Newport | | | | | | 2.1 |
| Parade | 5.6 | 6.5 | 5.0 | | 2.7 | |
| Park | | 5.7 | | 2.0 | 2.1 | |
| Ram I | 6.2 | 5.9 | 4.6 | 2.4 | | |
| Rugby | | | | 2.2 | | |
| Shasta | 5.7 | | | | | |
| Sydsport | 6.0 | 6.3 | 5.8 | | | 2.2 |
| Touchdown | 6.1 | 5.9 | 5.8 | | | |
| Trenton | | | | 2.4 | | |
| Vantage | 3.6 | 5.8 | 5.5 | 2.3 | 2.6 | 2.0 |
| Victa | 6.5 | 5.7 | 5.5 | 2.3 | 2.6 | 2.3 |
| Wabash | 4.8 | | | | | |

Rating Scale: Larger number indicates higher quality.

TABLE 12

Comparison of Turf Color of Ba 72-441 and Other Bluegrass Varieties at Various Locations in the U.S.A.

| Variety | St. Louis Missouri | Lincoln Nebraska | Marysville Ohio | Prince Frederick Maryland |
|---|---|---|---|---|
| Ba 72-441 | 9.1 | 7.0 | 8.3 | 7.5 |
| A-34 | | 6.5 | | |
| Adelphi | 9.4 | 7.2 | 8.4 | 7.8 |
| America | 9.4 | 7.0 | 8.5 | |
| Baron | 9.2 | 6.9 | 8.5 | 7.3 |
| Birka | 9.1 | 6.7 | 8.1 | 7.0 |
| Bonnieblue | | 7.0 | | 7.7 |
| Bono | 9.0 | | | 6.6 |
| Bristol | 9.5 | 7.3 | 8.9 | 7.4 |

TABLE 12-continued

Comparison of Turf Color of Ba 72-441 and Other Bluegrass Varieties at Various Locations in the U.S.A.

| Variety | St. Louis Missouri | Lincoln Nebraska | Marysville Ohio | Prince Frederick Maryland |
|---|---|---|---|---|
| Eclipse | | 7.0 | 8.5 | |
| Fylking | | 6.8 | | |
| Glade | 9.3 | 7.1 | 8.4 | |
| Kenblue | | | 8.1 | 5.9 |
| Merion | | 6.9 | | |
| Merit | 9.2 | 7.0 | | 6.8 |
| Midnight | | 7.9 | 8.9 | 7.4 |
| Newport | | | | |
| Parade | | 6.8 | | |
| Park | 9.0 | 6.1 | 8.1 | 6.6 |
| Ram I | | 7.3 | | 7.8 |
| Rugby | | 6.8 | | 7.9 |
| Sydsport | 9.2 | 7.0 | 8.2 | |
| Touchdown | 9.0 | 6.8 | 8.1 | |
| Vantage | 9.2 | 6.8 | 8.5 | 7.7 |
| Victa | 9.2 | 6.9 | 8.4 | 7.1 |
| Wabash | | | | 7.0 |
| LSD(.05) | 0.3 | — | — | — |

Rating Scale: Larger number indicates darker green color.

TABLE 13

Winter Color of Ba 72-441 and Other Bluegrass Varieties.

| Variety | Gervais, Oregon 2 Year Mean | Marysville, Ohio 1 Year Mean |
|---|---|---|
| Ba 72-441 | 4.8 | 2.7 |
| Adelphi | — | 2.0 |
| Bristol | 5.4 | 6.7 |
| Parade | — | 3.8 |
| Park | — | 1.2 |
| Vantage | — | 1.7 |
| Victa | 3.4 | 2.7 |
| LSD(.05) | 0.9 | — |

Rated 1-9: 9 = darkest green color.

TABLE 14

Spring Greening of Ba 72-441 and Other Bluegrass Varieties.

| | | Maryland | | Marysville, Ohio | |
|---|---|---|---|---|---|
| Variety | Lincoln Nebraska | Prince Frederick | Belts-ville | Test 1 | Test 2 |
| Ba 72-441 | 6.0 | 7.0 | 5.3 | 5.3 | 3.5 |
| A-34 | 5.0 | | 5.3 | | |
| Adelphi | 6.8 | 7.0 | 4.7 | 7.7 | 2.8 |
| America | 4.8 | | 4.7 | 6.3 | |
| Banff | | | 5.3 | | |
| Baron | 5.3 | 7.0 | 4.3 | 3.0 | |
| Birka | 5.0 | 7.3 | 4.7 | 5.7 | |
| Bonnieblue | 5.3 | 7.0 | | | |
| Bono | | 8.3 | | | |
| Bristol | 5.5 | 7.3 | 4.7 | 5.7 | 4.2 |
| Cheri | 4.8 | | 4.3 | | |
| Eclipse | 5.5 | | 5.7 | 6.5 | |
| Enmundi | 5.3 | | 4.7 | | |
| Fylking | 4.8 | | 4.7 | | |
| Geronimo | | | 6.3 | | |
| Glade | 5.3 | | 5.3 | 5.0 | |
| Kenblue | | 6.3 | 3.3 | 8.0 | |
| Merion | 5.0 | | 4.0 | | |
| Merit | 5.5 | 6.0 | 4.3 | | |
| Midnight | 4.8 | 7.0 | 4.7 | 2.0 | |
| Monopoly | | | 5.3 | | |
| Nassau | | | 7.7 | | |
| Nugget | | | 2.3 | | |
| Parade | 5.5 | | 4.3 | | 3.2 |
| Park | 5.8 | 6.0 | | 7.7 | 2.5 |
| Ram I | 5.5 | 7.7 | 6.5 | | |
| Rugby | 5.0 | 7.0 | | | |
| Shasta | | | 5.3 | | |
| Sydsport | 4.8 | | 4.7 | 5.3 | |
| Touchdown | 5.3 | | 4.3 | 5.7 | |
| Vantage | 5.8 | 7.7 | 5.0 | 8.0 | 3.0 |
| Victa | 5.8 | 5.7 | 3.7 | 4.3 | 3.0 |
| Wabash | | 6.7 | 5.3 | | |

TABLE 14-continued

Spring Greening of Ba 72-441 and Other Bluegrass Varieties.

| | | Maryland | | Marysville, Ohio | |
|---|---|---|---|---|---|
| Variety | Lincoln Nebraska | Prince Frederick | Belts-ville | Test 1 | Test 2 |
| LSD | 0.8 | 1.8 | | 1.6 | |

Rated 1-9: 9 = darkest green color.

Turf diseases are one of the major causes of inconsistent and poor turf performance among locations and years. Ba 72-441 has been found to have a high level of resistance to leaf spot (also known as melting out and crown rot) caused by *Helminthosporium vagans,* a medium to high level of resistance to rust caused by Puccinia spp., a medium level of resistance to dollarspot caused by *Sclerotina homeocarpa,* and a high level of resistance to stripe smut caused by *Ustilago striiformis.*

Resistance to stripe smut was determined in tests in Ohio and Maryland where Ba 72-441 and the standard varieties included in the tests had little or no incidence of stripe smut but several experimental selections were heavily infected. Comparisons of resistance to leaf spot, rust, and dollarspot are presented in Tables 15-17.

TABLE 15

Comparison of Leafspot Disease Incidence on Ba 72-441 and Other Bluegrasses at Several Locations in the U.S.A.

| | St. Louis[a] | Beltsville[b] | Adelphia[b] | Marysville, Ohio[a] | |
|---|---|---|---|---|---|
| Variety | Missouri | Maryland | New Jersey | Test 1 | Test 2 |
| Ba 72-441 | 2 | 8.0 | 8.0 | 6 | 42 |
| A-34 | | 5.3 | 4.3 | | |
| Adelphi | 2 | 8.0 | 5.7 | 9 | 75 |
| America | 8 | | | | 43 |
| Banff | | 5.3 | 7.0 | | |
| Baron | 2 | 7.0 | 8.7 | | 42 |
| Birka | 5 | | 6.3 | | 58 |
| Bonnieblue | | | 7.0 | | |
| Bono | 7 | | | | 63 |
| Bristol | 2 | 7.0 | 8.3 | 5 | 43 |
| Eclipse | | 7.7 | 9.0 | | 80 |
| Fylking | | 6.7 | 6.3 | | |
| Geary | | | 2.0 | | |
| Glade | 2 | 7.3 | 6.3 | | 38 |
| Kenblue | | 3.3 | 1.7 | | 93 |
| Merion | | 6.1 | 7.7 | | |
| Merit | 3 | 7.3 | 7.7 | | |
| Midnight | | 7.0 | 7.0 | | |
| Monopoly | | 5.3 | 6.0 | | |
| Nassau | | 7.7 | 7.4 | | |
| Parade | | 6.0 | 5.0 | 10 | |
| Park | 52 | | | 54 | 95 |
| Ram I | | 6.5 | 7.0 | | |
| Rugby | | | 5.0 | | |
| Shasta | | | 6.0 | | |
| Sydsport | 3 | 7.3 | 6.3 | | 48 |
| Touchdown | 7 | 7.7 | | | 57 |
| Trenton | | | 6.0 | | |
| Vantage | 7 | 5.0 | 2.0 | 15 | 90 |
| Victa | 2 | 8.0 | 7.0 | 7 | 22 |
| Wabash | | | 2.0 | | |
| LSD(.05) | 7 | | 1.9 | | 34 |

Ratings
[a]% of turf affected by disease.
[b]1-9: 9 = least disease.

TABLE 16

Comparison of Rust (Puccinia spp.) Disease Incidence on Ba 72-441 and Other Bluegrasses.

| | Adelphia[a] | Gervais, Oregon | |
|---|---|---|---|
| Variety | New Jersey | Turf[b] | Seed Production[c] |
| Ba 72-441 | 7.0 | 43 | 2.0 |
| Adelphi | 7.1 | | |
| America | 7.4 | | |

TABLE 16-continued

Comparison of Rust (Puccinia spp.) Disease Incidence on Ba 72-441 and Other Bluegrasses.

| Variety | Adelphia[a] New Jersey | Gervais, Oregon Turf[b] | Gervais, Oregon Seed Production[c] |
|---|---|---|---|
| Banff | 6.5 | | |
| Baron | 6.4 | | |
| Birka | 3.5 | | |
| Bonnieblue | 5.4 | | |
| Bristol | 7.7 | 7 | 4.0 |
| Eclipse | 4.7 | | |
| Julia | | | 4.0 |
| Merion | 2.4 | | |
| Merit | 5.7 | | |
| Midnight | 7.0 | | |
| Monopoly | 7.1 | | |
| Mosa | | | 4.0 |
| Nassau | 6.8 | | |
| Newport | | | 4.0 |
| Parade | 6.2 | | |
| Ram I | 7.0 | | |
| Touchdown | 3.5 | | |
| Vantage | 6.2 | | |
| Victa | 5.6 | 63 | 2.0 |
| LSD(.05) | 0.9 | | |

Ratings:
[a]Stem Rust (*Puccinia graminis* Pers.)0–9: 9 = no disease.
[b]% of turf affected by disease.
[c]1–4: 4 = very susceptible.

TABLE 17

Comparison of Dollarspot Disease Incidence on Ba 72-441 and Other Bluegrasses.

| Variety | Prince Frederick Maryland | Marysville Ohio |
|---|---|---|
| Ba 72-441 | 15 | 27 |
| Adelphi | 8 | 20 |
| America | | 13 |
| Baron | 50 | 23 |
| Birka | 6 | 47 |
| Bonnieblue | 10 | |
| Bono | 4 | 63 |
| Bristol | 6 | 17 |
| Eclipse | | 8 |
| Glade | | 40 |
| Kenblue | 8 | 37 |
| Merit | 4 | |
| Midnight | 6 | |
| Park | | 33 |
| Ram I | 40 | |
| Rugby | 12 | |
| Sydsport | | 43 |
| Touchdown | | 50 |
| Trenton | 28 | |
| Vantage | 11 | 15 |
| Victa | 5 | 23 |
| Wabash | 11 | |
| LSD(.05) | 19 | 24 |

Rating: % of turf affected by disease.

Ba 72-441 has the capability to tolerate heat and drought stress. In addition, it has a low growth habit and a slower vertical growth rate than many varieties, especially the common type of varieties such as Park, Newport, and Kenblue, that should allow it to tolerate lower mowing heights and possibly decrease the total number of mowings per year without sacrificing overall turf performance. The leaf texture of the new variety is similar to many bluegrass varieties when maintained under mowed turf conditions. Comparisons showing tolerance to drought and heat stress, growth habit, and leaf texture are presented in Tables 18–20.

TABLE 18

Comparison of Drought and Heat Tolerance of Ba 72-441 and Other Bluegrasses.

| Variety | Prince Frederick Maryland | Marysville Ohio |
|---|---|---|
| Ba 72-441 | 2 | 1 |
| Adelphi | 12 | 18 |
| Baron | 10 | |
| Birka | 5 | |
| Bonnieblue | 4 | |
| Bono | 13 | |
| Bristol | 11 | 8 |
| Kenblue | 15 | |
| Merit | 7 | |
| Midnight | 13 | |
| Parade | | 27 |
| Park | 7 | 13 |
| Ram I | 6 | |
| Rugby | 9 | |
| Vantage | 10 | 8 |
| Victa | 9 | 13 |
| Wabash | 9 | |

Rated as % turf losing healthy green color.

TABLE 19

Comparison of Growth Habit of Ba 72-441 and Other Bluegrass Varieties Under Mowed Conditions at Marysville, Ohio.

| Variety | Test 1[a] Year 1 | Test 1[a] Year 2 | Test 2[b] |
|---|---|---|---|
| Ba 72-441 | 79 | 61 | 1.7 |
| Adelphi | | | 2.7 |
| Bristol | 69 | 73 | 2.0 |
| Fylking | 95 | 80 | |
| Kenblue | 96 | 81 | |
| Merion | 76 | 71 | |
| Merit | 86 | 76 | |
| Newport | 92 | 78 | |
| Parade | | | 2.3 |
| Park | | | 2.3 |
| Sydsport | 70 | 64 | |
| Vantage | 85 | 65 | 2.0 |
| Victa | 81 | 64 | 2.0 |
| LSD(.05) | 15 | 13 | 0.6 |

Rating:
[a]Height (mm) of turf about one week after last mowing.
[b]0–9: 9 = very tall growing turf, 0 = no growth since last mowing.

TABLE 20

Comparison of Leaf Texture of Ba 72-441 and Other Bluegrasses Under Mowed Turf Conditions.

| Variety | St. Louis Missouri | Marysville Ohio |
|---|---|---|
| Ba 72-441 | 4.6 | 5.0 |
| Adelphi | 5.3 | |
| America | 6.0 | |
| Baron | 4.6 | |
| Birka | 6.0 | |
| Bono | 5.6 | |
| Bristol | 5.3 | 5.0 |
| Fylking | | 5.8 |
| Glade | 6.0 | |
| Kenblue | | 5.5 |
| Merion | | 5.0 |
| Merit | 4.3 | 5.0 |
| Newport | | 5.0 |
| Park | 6.0 | |
| Sydsport | 5.0 | 5.0 |
| Touchdown | 5.0 | |
| Vantage | 6.0 | 5.3 |
| Victa | 4.4 | 4.8 |
| LSD(.05) | 0.7 | 0.4 |

Rating: 1–9: 9 = narrowest leaf blade.

The new variety has a very high level of seed yielding potential which will make it economical to produce and aid in its commercial success. Comparative results on seed yield are shown in Table 21.

TABLE 21

Seed Yield Comparisons of Ba 72-441 and Other Bluegrass Varieties in Oregon.

| Location | Gervais | | | LaGrande | | |
|---|---|---|---|---|---|---|
| Harvest Year | Year 1 | Year 2 | Mean | Year 1 | Year 2 | Mean |
| Variety | | | | | | |
| Ba 72-441 | 691 | 1586 | 1139 | 1512 | 1253 | 1383 |
| Victa | 780 | 1394 | 1087 | 1419 | 1200 | 1310 |
| Newport | 435 | 1256 | 846 | | | |
| Bristol | 347 | 808 | 578 | 1089 | 970 | 1030 |

TABLE 21-continued

Seed Yield Comparisons of Ba 72-441 and Other Bluegrass Varieties in Oregon.

| Location | Gervais | | | LaGrande | | |
|---|---|---|---|---|---|---|
| Harvest Year | Year 1 | Year 2 | Mean | Year 1 | Year 2 | Mean |
| Mosa | 322 | 1060 | 691 | | | |
| Julia | 296 | 1016 | 656 | | | |
| LSD(.05) | 140 | 134 | | 149 | 181 | 220 |

Rating: Pounds per acre of conditioned seed.

What is claimed is:

1. A variety of Kentucky bluegrass plant, substantially as shown and described, characterized by a high level of resistance to disease, especially leaf spot disease, a desirable green color throughout the growing season, a high quality persistent turf under a wide variety of environmental conditions and a very high level of seed yielding capacity.

* * * * *